US00PP13520P2

(12) United States Plant Patent
Lemon

(10) Patent No.: US PP13,520 P2
(45) Date of Patent: Jan. 28, 2003

(54) GERANIUM PLANT NAMED 'ELEGANCE RASPBERRY SWIRL'

(75) Inventor: David Lemon, County of Santa Barbara, CA (US)

(73) Assignee: Olgevee, Ltd., Connellsville, PA (US)

( * ) Notice: Subject to any disclaimer, the term of this patent is extended or adjusted under 35 U.S.C. 154(b) by 0 days.

(21) Appl. No.: 09/876,817

(22) Filed: Jun. 7, 2001

(51) Int. Cl.[7] ..... A01H 5/00

(52) U.S. Cl. ..... Plt./331

(58) Field of Search ..... Plt./331

*Primary Examiner*—Bruce R. Campell
*Assistant Examiner*—A Para
(74) *Attorney, Agent, or Firm*—Webb Ziesenheim Logsdon Orkin & Hanson, P.C.

(57) ABSTRACT

A new and distinct early flowering regal geranium plant with striking shades of deep raspberry and electric pink on the upper petals and a delicate pink blush on the lower petals above medium green foliage.

1 Drawing Sheet

CLASSIFICATION

*Pelargonium×domesticum* (regal geranium).

VARIETAL DENOMINATION

'Elegance Raspberry Swirl'.

BACKGROUND OF THE INVENTION

The present invention comprises a new and distinct cultivar of *Pelargonium×domesticum* known by the varietal name 'Elegance Raspberry Swirl'. The new variety was discovered in a selected breeding program in Connellsville, Pa., Breeder No. 6DG3081-6. The new variety is a selection from the cross of unpatented proprietary breed variety Seedling Pink/Blotch #262, the female parent and unpatented proprietary breed variety Seedling Salmon/Blotch #266, the male parent. The new variety exhibits similar flower color to the female parent and is more vigorous, more free flowering, and blooms earlier than both parents. The red and white bicolor of the flowers of the new variety is distinct from other varieties in this market class. The new variety was first asexually reproduced by cuttings in Connellsville, Pa. The new variety has been trial and field tested at Connellsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of 13 weeks from a rooted cutting to flowering in a 6 inch pot. The response time was determined on plants grown in soilless media employing constant fertilizer 150–200 parts per million of nitrogen and potassium in full light.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar at 10 weeks grown from a rooted cutting. The data which defines these characteristics were collected by asexual reproductions carried out by Oglevee, Ltd. in Connellsville, Pa. The color readings were taken Jan. 4, 2001 on a plant under 200–220 foot candles of fluorescent cool white light. Color references are primarily to The R.H.S. Colour Chart of The Royal Horticultural Society of London.

PLANT

Form: Trailing, cascading mound.
Height: 13–18 cm from soil to top of foliage.
Growth: Upright, free basal branching.
Strength: Does not require artificial support.
Foliage: Stalked leaf attachment; medium green foliage.
Rooting time: Roots visible to outside of artificial dirt plug in 14–21 days.
Leaves:
- *Size.*—Length: 7.0–7.5 cm.
- *Width.*—9.5–11.5 cm.
- *Shape.*—Reniform; truncate base.
- *Margin.*—Crenate.
- *Texture.*—Leathery; pubescent.
- *Color.*—Upper surface: Green Group 137A. Lower surface: Green Group 138B.
- *Ribs and veins.*—Venation: Palmate. Color: Yellow-Green Group 145C.

Petioles:
- *Color.*—Yellow-Green Group 144A.
- *Length.*—6.5–7.5 cm.

Stem:
- *Color.*—Yellow-Green Group 144A.
- *Internode length.*—1.3–1.7 cm.

THE BUD

Shape when just showing color:
- *Overall.*—Inverted bowl shape.
- *Individual bud.*—Elliptical.

Size:
- *Overall.*—3.7–4.0 cm across.
- *Individual bud.*—1.7–2.0 cm long; 0.7–1.0 cm wide.

Number of buds per cluster: 9.

INFLORESCENCE

Blooming habit: Continuous flowering.

*Size.*—15.5–16.0 cm.

*Borne.*—Flowers on pedicel; pedicel on peduncle; 3–7 cm above foliage.

Flowers:

*Form.*—Slightly cupped; petals overlap; ruffled.

*Number of flowers per umbel.*—5–7.

*Size.*—Diameter: 7.0–8.0 cm. Depth: 3.5–4.0 cm.

Petals:

*Color.*—The upper petals consist of two or three petals with a large "eye" and the lower petals consist of three petals with no eye. Upper surface: Lower Petals: Delicate pink shade of Red Groups 56C and 56B. Halfway down the length of the petal this pink shade blushes into white. In the middle of the petal is a small area of red-pink that can be Red Group 52C with small specks of Red Group 52B, or can be slightly darker with shades that include Red Group 51A, Red Groups 53C and 53D, and darker areas on top of that of Red Groups 53B and 53A. Sometimes there are small streaks of color as dark as Greyed-Purple Group 187A. Upper Petals: At the very outer edge of the petal is a thin area approximately 0.4 cm in width of Red Group 56D. Then the blotch begins at outermost edge it is Red Group 52C moving to Red Group 52B and then into darker shades Red Group 53D, Red Group 53C, Red Group 53B and Red Group 53A. Also included in the very dark eye area is Greyed-Purple Groups 187A and 187B. The base of the petal is white with dark veining of varying degrees of purple shades. The darkest purple shade is Greyed-Purple Group 187B and is found closest to the blotch near the center of the petal and throughout the eye. Several shades of slightly lighter purple are found towards the base of the petal, the colors are Red-Purple Group 71A and Red-Purple Group 70A. Some of the veining starts at the base of the petal and is streaked out in an arc-type pattern, within the streak the color changes from the purples mentioned above to Red-Purple Group 61B, Red-Purple Group 60B, Red-Purple Group 67B, Red-Purple Group 66B, and Red Group 52A. Sometimes veining of Red Group 53A is present. At some places on the dark eye small flecks of a silvery color appear. These flecks are composed of Grey Group 201D and Greyed-Purple Group 186D. Lower surface: Lower Petals: White at base with an area of pale pink, Red Groups 56C and 56D around the outer edge. Darker area in center shows through and is Red-Purple Group 67A, or lighter of Red Group 52C. Upper Petals: Majority of the base of the petal is white. Toward the center the blotch shows through and contains colors that include Red-Purple Group 71A, Red-Purple Group 67A, Red-Purple Group 64A, Red-Purple Group 61A, Red-Purple Group 59A, and toward the outer edge bright fluorescent shades of pink that include Red-Purple Group 61C, and Red-Purple Group 57B. Dark veining of Red-Purple Groups 64A, 64B, and 64C are also present.

*Shape.*—Obovate.

*Size.*—4.0–5.0 cm.

*Margin.*—Entire.

*Number per floret.*—5–6.

Texture and appearance: Reflective, smooth, velvety.

Tonality from a distance: Striking shades of deep raspberry and electric pink are found on the upper petals with a delicate pink blush color on the lower petals.

Petaloids: None observed.

Pedicel:

*Length.*—1.5–2.3 cm.

*Color.*—Yellow-Green Group 144A.

Peduncle:

*Length.*—7.5–8.5 cm.

*Color.*—Yellow-Green Group 144A.

Disease/pest resistance: No unusual susceptibility to diseases or pests has been noted to date.

Fragrance: None.

REPRODUCTIVE ORGANS

Stamens:

*Quantity.*—7.

*Anthers.*—0.5 cm.

*Filaments.*—Length: 1.0–1.6 cm. Color: White. Pollen: Golden orange.

Pistils:

*Number.*—One.

*Length.*—1.5–2.0 cm.

*Stigma.*—Number: One. Color: Orchid purple.

*Style.*—Length: 1.0 cm. Color: Orchid purple.

Ovaries:

*Completeness.*—Superior.

*Pubescence.*—Very pubescent.

*Length.*—0.7–0.8 cm.

*Width.*—0.25–0.3 cm.

*Color.*—Green.

Fruit: None observed.

I claim:

1. A new and distinct variety of geranium plant substantially as shown and described.

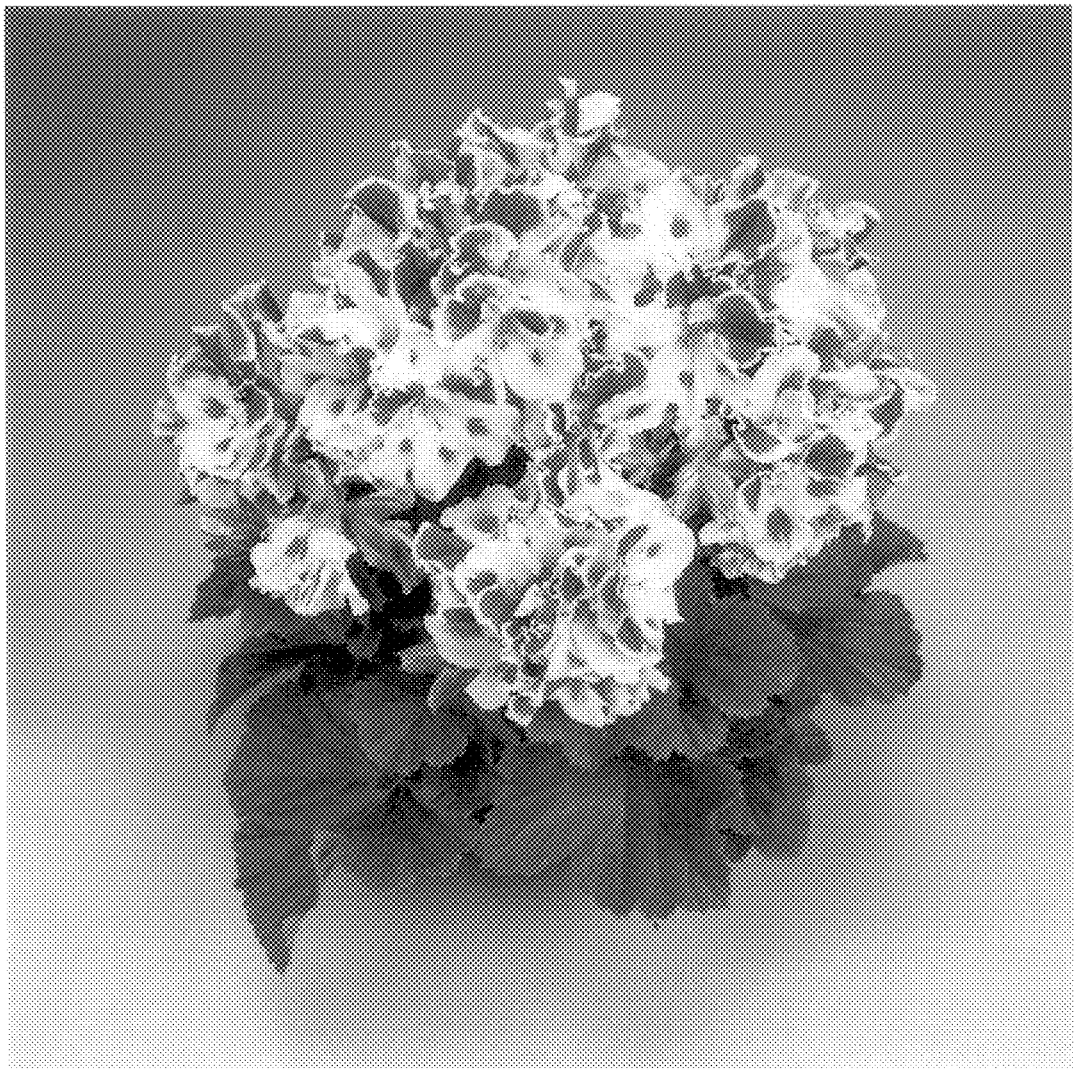

* * * * *